(12) United States Patent  
Geistert

(10) Patent No.: US 9,339,269 B2  
(45) Date of Patent: May 17, 2016

(54) DEVICE FOR EXPLANTING ELECTRODE LEADS

(71) Applicant: VascoMed GmbH, Binzen (DE)

(72) Inventor: Wolfgang Geistert, Rheinfelden (DE)

(73) Assignee: VascoMed GmbH, Binzen (DE)

( * ) Notice: Subject to any disclaimer, the term of this patent is extended or adjusted under 35 U.S.C. 154(b) by 657 days.

(21) Appl. No.: 13/665,109

(22) Filed: Oct. 31, 2012

(65) Prior Publication Data

US 2013/0116704 A1    May 9, 2013

Related U.S. Application Data

(60) Provisional application No. 61/588,183, filed on Jan. 19, 2012.

(30) Foreign Application Priority Data

Nov. 3, 2011    (DE) .......................... 10 2011 085 683

(51) Int. Cl.
*A61B 19/00* (2006.01)
*A61B 17/064* (2006.01)
*A61B 17/34* (2006.01)
(Continued)

(52) U.S. Cl.
CPC ......... *A61B 17/0642* (2013.01); *A61B 17/0682* (2013.01); *A61B 17/3468* (2013.01); *A61B 2017/0641* (2013.01); *A61N 1/05* (2013.01)

(58) Field of Classification Search
CPC ... A61N 1/057; A61N 1/0539; A61N 1/0558; A61N 1/0573; A61N 1/059; A61N 2001/0578; A61N 2001/058; A61N 2001/0582; A61B 17/320725; A61B 5/042; A61B 5/0421; A61B 5/0422; A61B 17/34; A61B 17/3415; A61B 17/3417; A61B 17/3421; A61B 17/3423; A61B 17/3426; A61B 17/3468; A61B 17/3476; A61B 17/3478; A61B 17/3496; A61B 2017/3419; A61B 2017/3435; A61B 2017/3441; A61B 2017/345; A61B 2017/3454

USPC .......................... 606/129, 108; 607/115–117

See application file for complete search history.

(56) References Cited

U.S. PATENT DOCUMENTS 4,576,162 A     3/1986  McCorkle
4,582,056 A *   4/1986  McCorkle, Jr. ................... 606/1
(Continued)

OTHER PUBLICATIONS

European Search Report and Notes to the European Search Report on European Patent Application No. EP 12 18 9858, dated Feb. 8, 2013 (11 pages).

*Primary Examiner* — Katrina Stransky
*Assistant Examiner* — Katherine Schwiker
(74) *Attorney, Agent, or Firm* — Buchanan Ingersoll & Rooney PC

(57) ABSTRACT

An explantation device for explanting implanted leads, having a distal end pointing in the direction of the explantation site and a proximal end pointing in the direction of the surgeon. The explantation tool comprising a locking sheath comprising a hose-like or tubular body having a lumen along a longitudinal axis and at least one clamping device at or in the vicinity of the distal end; and a cutting sheath for removing adhering tissue, having a proximal and a distal end and comprising a hose-like or tubular body having a lumen along a longitudinal axis and a detaching unit at or in the vicinity of the distal end; wherein the cutting sheath comprises at least one receptacle for the clamping device of the locking sheath.

8 Claims, 6 Drawing Sheets

(51) Int. Cl.
  *A61B 17/068* (2006.01)
  *A61N 1/05* (2006.01)

(56) References Cited

U.S. PATENT DOCUMENTS 5,697,936 A * 12/1997 Shipko et al. ............ 606/108
5,779,715 A 7/1998 Tu
6,033,402 A 3/2000 Tu et al.
6,358,256 B1 3/2002 Reinhardt
2005/0192591 A1 9/2005 Lui et al.
2006/0116689 A1 6/2006 Albans et al.
2008/0255597 A1 10/2008 Pravong et al.
2010/0198229 A1 8/2010 Olomutzki et al.
2011/0106099 A1 5/2011 Duffy et al.

* cited by examiner

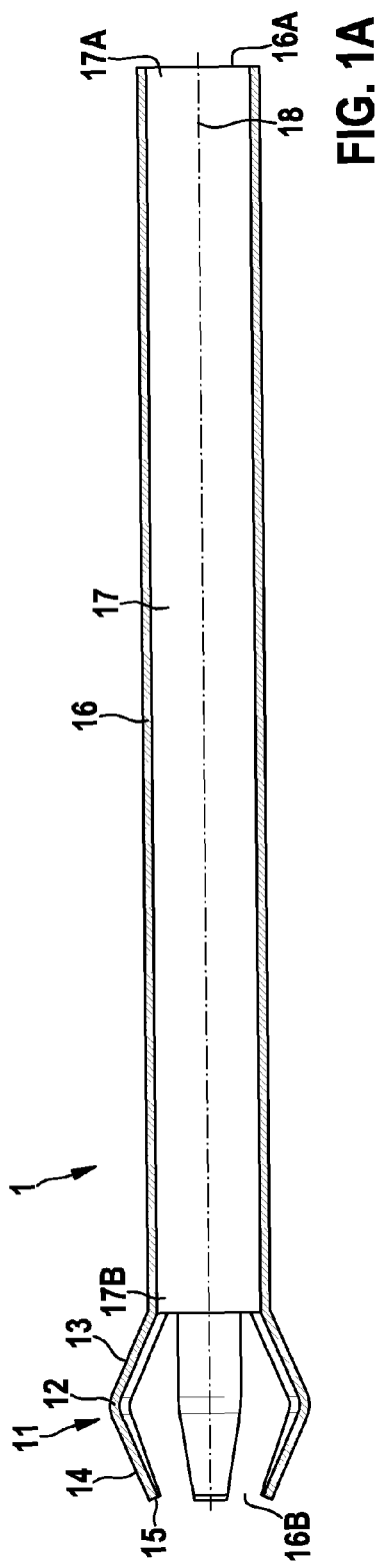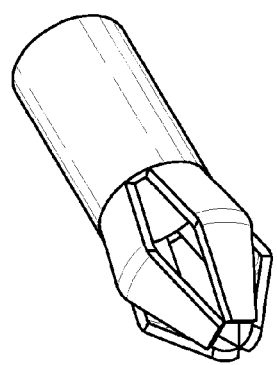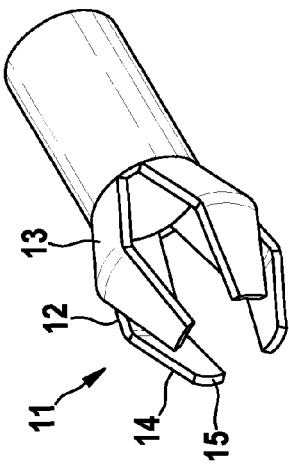

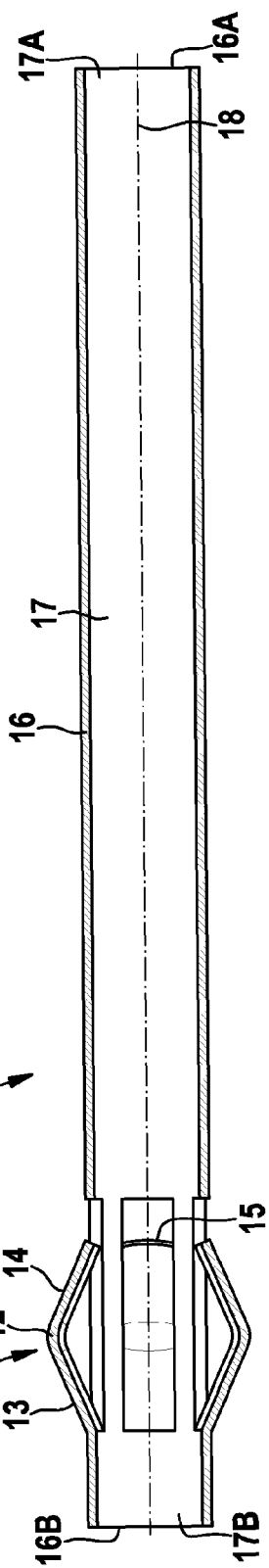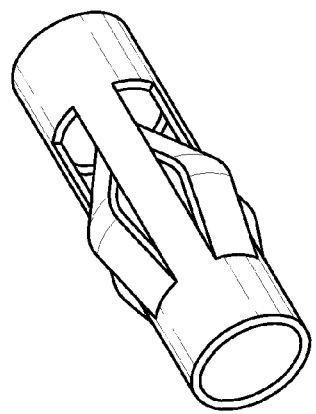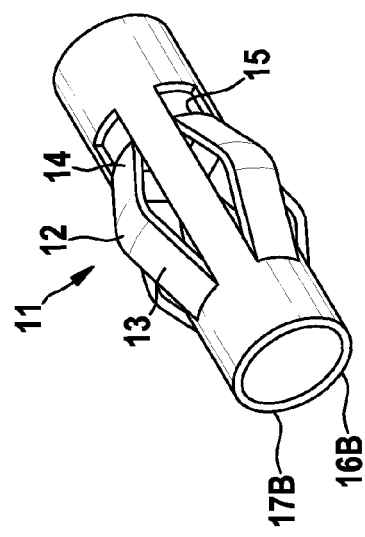

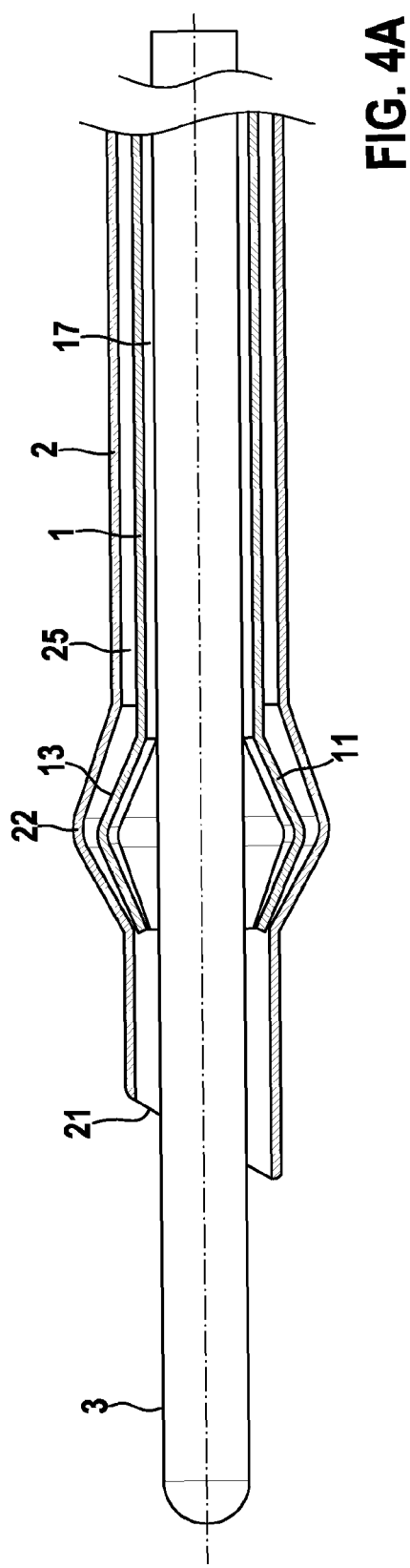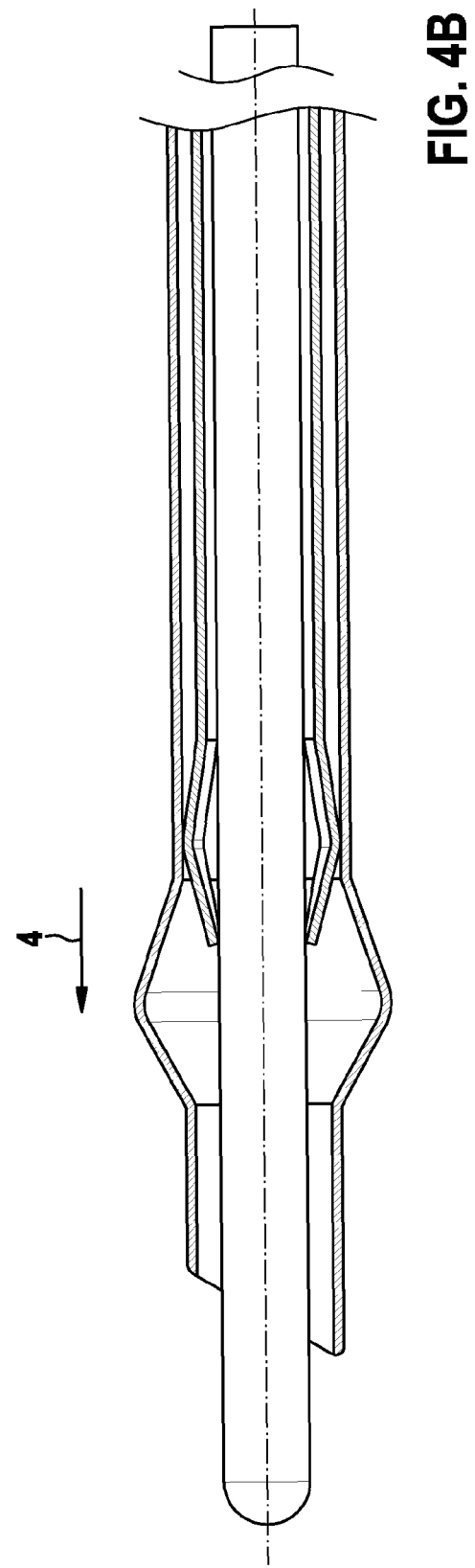

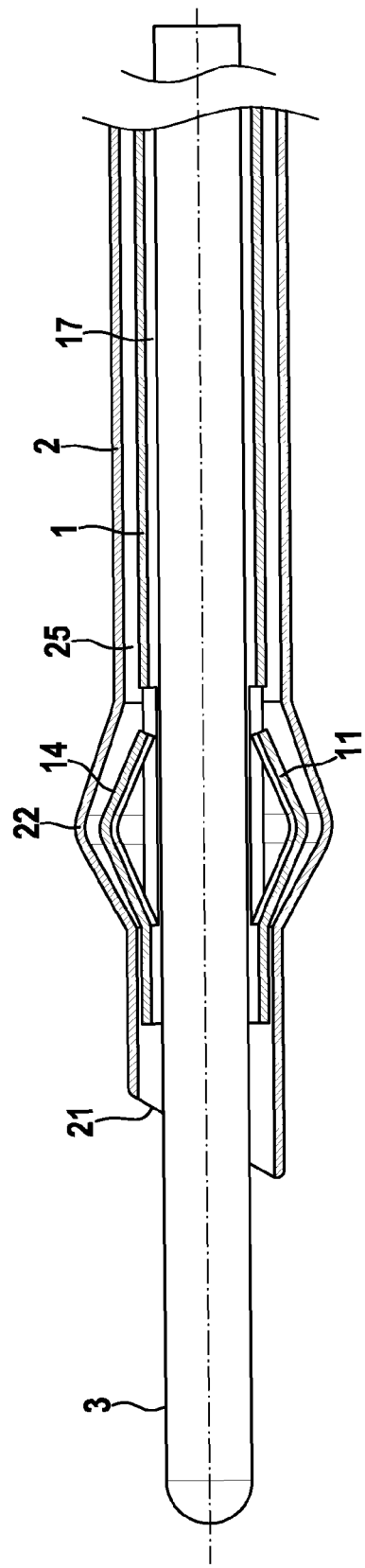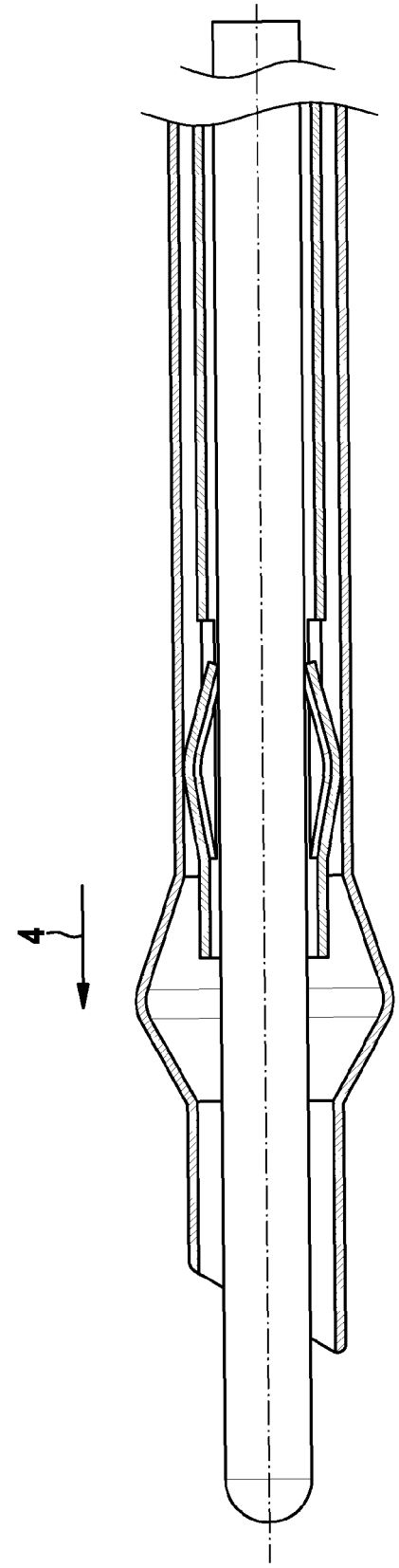

DEVICE FOR EXPLANTING ELECTRODE LEADS

CROSS-REFERENCE TO RELATED APPLICATIONS

This application claims the priority of German Patent Application No. DE 10 2011 085 683.8, filed on Nov. 3, 2011 in the German Patent Office and U.S. Provisional Patent Application No. 61/588,183, filed on Jan. 19, 2012 in the U.S. Patent Office, the disclosures of which are incorporated herein in their entirety by reference.

TECHNICAL FIELD

The patent application relates to a device for explanting implanted leads.

BACKGROUND

The use of implantable leads has been known for quite some time in medicine. Implantable leads are used in particular to connect electrical implants—generally cardiac pacemakers, defibrillators, cardioverters, and the like—to the site to be treated electromedically. In the field of application that has been known for a long time, this site is often the heart, on or in which the implantable leads are attached. Meanwhile, implantable leads which lead into the heart and are routed, for example, through the right atrium into the atrial appendage or into the apex of the right ventricle and are fixed there either by passive anchorings—known as "tines"—or by being screwed into the cardiac tissue, have become established. With certain indications, such implantable leads are also routed through the atrium of the heart into the coronary sinus (a coronary vessel, also referred to in short as "CS"), so as to conduct a therapy there on the left side of the heart.

All implantable leads mentioned and/or described in this patent application generally comprise an elongated electrode body, at the distal end of which, in addition to the aforementioned exemplary fixation options, at least one electrode pole is present, which delivers therapeutic signals and/or senses physiological signals. At the proximal end of the electrode body, located opposite of the distal end, at least one connector system is present, by which the implantable lead is connected to the electrical implant. Hereinafter, "distal" shall mean pointing in the direction of the explantation site and "proximal" shall mean pointing in the direction of the surgeon. Electrical connecting lines, by which the at least one electrode pole at the distal end is electrically connected to the connector system at the proximal end, run in the electrode body in the longitudinal direction. Moreover, the implantable lead can have a generally centrally extending continuous lumen, which at the proximal end, and optionally at the distal end, is connected to the surroundings. This lumen is used to guide the implantable lead along a previously placed guide wire, or by way of a mandrin. The electrode body can also comprise other elements, however, these will not be addressed here in detail.

Immediately after implanting an implantable lead, a natural process sets in which ensures adhesion of the implantable lead. To this end, generally tissue grows around the lead, at least on the electrode tip, which results in fixation. However, it is also possible for the implantable lead to experience adhesion not only at the tip, but in an undefined manner at the electrode body thereof, for example, in sites in which the implantable lead is in contact with the surrounding vascular or cardiac tissue. This adhesion process generally results in the implantable lead, which is made of material foreign to the body, not undergoing any rejection reaction.

From the view of a person skilled in the art or health professional, the disadvantage of this natural adhesion process is that the explantation of an implanted lead of the aforementioned type is very difficult, and at times even impossible. These explantations are quite often life-threatening for the patient.

Explantations are required, for example, when the implanted lead is defective, whereby no reliable stimulation or measured value recording is possible any longer. This can result in severe and life-threatening malfunctions of the electrical implant. Given the complexity and danger to life of an explantation, many physicians in the past decided to simply leave defective electrodes in the body without them having any function, instead of explanting them, and to run new functional implantable leads into the heart.

However, indications also exist in which a physician has no options and the implanted lead must be explanted in any case. Examples include infections of what is known as the pacemaker pocket—this is how the implantation site of the implant is referred to—or sepsis along the implanted lead. In these instances, the infection site must be removed as quickly as possible, resulting in inevitable explantation of the implanted lead.

A variety of aids are known in order to facilitate or enable the explantation of the implanted lead in these instances. Notably, cutting tools—also referred to as cutting sheaths—are known. These generally involve a hose-like or tubular body having a lumen and a proximal and a distal end, wherein the distal end comprises a detaching unit. For explanation purposes, this cutting sheath is guided over the implanted lead and pushed forward to the distal end of the lead. The detaching unit then has a detaching effect on the tissue adhering around the implanted lead. Detaching units are known from the prior art of cutters, which detach or "scrape" the tissue from the implanted lead by means of a blade pointing in the distal direction. A cutting sheath comprising such a detaching unit is technically simple, but it is not the most effective means for removing tissue from a grown-in implanted lead.

Detaching units operating based on high-frequency or laser technology are also known from the prior art. Such detaching units are technically so complex that the error rate in terms of use is very high. Another reason for this high error rate is that use is not easy and the physician loses any sensation as a result of this "active" cutting technique.

All of the aforementioned solutions, moreover, require the use of an opposing force, which is applied by anchoring what is known as a locking stylet at the distal end of the implanted lead. In order to apply the opposing force, the locking stylet is introduced into the central lumen of the implanted lead, advanced to the distal end of the implanted lead, and clamped there so that the implanted lead can no longer move with respect to the locking stylet. Thereafter, the stylet is fixed outside of the body and the cutting sheath comprising the detaching unit is displaced relative to the implanted lead with the locking stylet. The implanted lead is thereby fixed and acts counter to the cutting force directed in the direction of the distal end of the implanted lead. An example of such a locking stylet is described in U.S. Pat. No. 6,358,256.

Locking stylets have several disadvantages. For one, the use of such a stylet is always dependent on the presence of a central lumen. However, newer implantable leads, especially those for use in the CS or neural leads, frequently no longer have a central lumen. Secondly, it is advantageous to always position the application site for the opposing force in the vicinity of the detaching unit, which can be displaced relative to the implanted lead. With a locking stylet, however, releasing the clamping and repositioning with respect to the detaching unit on the cutting sheath are not possible. This often results in major problems when removing tissue in the more proximal region of the implanted lead because the implantable lead is very soft and flexible there, and the opposing force cannot always be directly transmitted. Moreover, it is important for the implanted lead not to undergo any change of the outer circumference so as to detach the implanted lead with only the necessary damage to the tissue.

A "locking sheath" according to the prior art is a refinement of the locking stylet and is likewise used to apply a force that opposes the cutting force. This locking sheath generally comprises a hose-like or tubular body having a lumen along a longitudinal axis and a distal and a proximal end. At the distal end, the locking sheath comprises a clamping device, the clamping direction of which acts radially in the direction of the longitudinal axis. For explantation purposes, the locking sheath is guided over the implanted lead and advanced to the adhesion. There, the clamping device is released, which is to say it acts in the direction of the implanted lead and clamps the implanted lead so that the implanted lead can no longer move with respect to the locking sheath. Thereafter, the locking sheath is fixed outside of the body and the cutting sheath comprising the detaching unit is displaced relative to the locking sheath with the implanted lead. The implanted lead is thereby fixed and acts counter to the cutting force directed in the direction of the distal end of the implanted lead. An example of such a locking sheath is described in U.S. Pat. No. 4,576,162.

The disadvantage of the solution described therein is that the distal end of the locking sheath located between the cutting sheath and the implanted lead has to be pushed out of the distal end of the cutting sheath to remove tension from the clamping device. This is unfavorable because no blade is present at the locking sheath. This means that the adhesion can be penetrated only to a limited extent, which requires multiple readjustments during the procedure. Moreover, the implanted lead is always fixed during the cutting operation, which may not be desirable in some circumstances.

According to a further embodiment of the prior art locking sheath, a detaching unit can also be arranged at the distal end. An example of this is provided in document U.S. Publication No. 2010/0198229. There, clamping is carried out at the proximal end by means of hydraulics. Hydraulic clamping, however, is complex to implement and difficult to handle manually.

It is therefore an object of the present patent application to provide a technically simple explantation device for implanted leads which is easy to use and offers improved fixation options, and a method for the use thereof.

The present application is directed toward overcoming one or more of the above-identified problems.

SUMMARY

An object of the present application is achieved by a device for explanting implanted leads, comprising a distal end and a proximal end according to the independent claim(s). The dependent claims describe further inventive embodiments.

The explantation device comprises a locking sheath for releasably fastening to an implanted lead, the locking sheath comprising a distal and a proximal end and further comprising a hose-like or tubular body having a lumen along a longitudinal axis, the lumen having an opening both at the distal end and at the proximal end, and at least one clamping device at or in the vicinity of the distal end which can be transferred from a relaxed state into a clamped state and, back into the relaxed state. The explantation device further contains a cutting sheath for removing adhering tissue, the cutting sheath comprising a proximal and a distal end and likewise comprising a hose-like or tubular body having a lumen along a longitudinal axis, the lumen having an opening both at the proximal end and at the distal end, and a detaching unit at or in the vicinity of the distal end, wherein the cutting sheath can be moved freely in relation to the locking sheath along the longitudinal axis. The explantation device is characterized in that the cutting sheath comprises at least one receptacle for the clamping device of the locking sheath, the receptacle being designed so as to receive the clamping device therein in the relaxed state.

This solution is based on the conclusion that it is useful to have a universal extraction device that can be applied for all kinds of implantable leads, which is to say also for implantable leads having no central lumen. In addition, the realization has become established that it is very important to have a technically simple device, which allows little erroneous handling during use and causes few technical defects because of the technical simplicity. By applying the opposing force directly at the detachment site of the tissue, the effectiveness of the extraction process is significantly improved.

The above solution is thus a highly effective extraction device, which simplifies and refines the extraction of implanted leads.

In the clamped state of an embodiment of the above solution, the at least one clamping device fixes the locking sheath to the implanted lead and, in the relaxed state, releases the fixation to the implanted lead, wherein the transfer from the relaxed state to the clamped state, and from the clamped state to the relaxed state, takes place by displacing the cutting sheath, and hence the at least one receptacle, along the longitudinal axis in relation to the locking sheath, so that the at least one clamping device moves out of or into the at least one receptacle. This simplifies handling even further, and inadvertent detachment of the implanted lead during the detaching process is thus prevented.

Preferably, the clamping device of the explantation device can be transferred from a relaxed state into a clamped state and/or back into the relaxed state by way of a spring force. Alternatively possible are other mechanisms which lead to a reversible clamping state or a transfer from a relaxed state into a clamped state and/or back into a relaxed state.

The advantage is that the locking sheath can be guided together with the cutting sheath along the implanted lead when the at least one clamping device is present in the at least one receptacle. It is also possible for the joint guidance of the locking and cutting sheaths to be carried out only temporarily, which is to say that the cutting sheath is introduced into the body after the locking sheath.

For this purpose, in one embodiment, the at least one clamping device and the at least one receptacle can have at least one respective radial extension component. In this case, the radial extension component has a direction pointing substantially away from the longitudinal axis of the explantation device.

If the clamping device is in the relaxed state, in which it does not exert any clamping force on the implanted lead, the explantation device can be displaced independently of the implanted lead. In this state, it can be either advanced in the distal direction or pulled out over the implanted lead. This makes the work of the surgeon even easier, who can thus concentrate entirely on the dangerous explantation process and is not burdened by the complicated handling of the explantation device. However, if the clamping device is not located in the receptacle and is in the clamped state, displacement of the implanted lead is no longer possible. In this state, an opposing force acts and the detachment of difficult adhesions is possible. In this state, the implanted lead can be "pulled", which is to say it can be explanted from the body by means of the explantation device and after complete removal of the tissue.

It is then preferably also conceivable for the at least one clamping device to be a collet, which comprises at least one, and preferably four, clamping links extending in the direction of the longitudinal axis, wherein each clamping link comprises a first section, which is attached at a first end to the locking sheath, and a second section having an end projecting radially in the direction of the longitudinal axis. According to a possible additional embodiment, the clamping links extend parallel to each other in the direction of the longitudinal axis.

It is particularly preferred for the first section of the clamping links, in the relaxed state, to have an extension component that from the first end of the section toward a second end is directed radially away from the longitudinal axis, and for the second section, which is provided at the second end of the first section, to have an extension component that is directed toward the inwardly projecting end and radially toward the longitudinal axis. This gives the clamping device a radially outwardly directed curvature, in which it is located in the likewise outwardly curved receptacle.

If the cutting sheath is now displaced in relation to the locking sheath, the clamping device is transferred into the clamped state, so that the inner end still more preferably projects into the lumen of the locking sheath. The clamping device can thus exert a clamping force on the implanted lead. This embodiment also allows the surgeon to carry out the clamping by a purely passive actuation and without additional aids, and without losing focus of the actual detachment of the implanted lead.

The inwardly projecting end is shaped so as to assure secure fixation without the possibility of sliding. For this purpose, it can be rounded toward the inwardly projecting end, and it can be ground in an angled manner, be roughened and ground, and ground as a blade, and/or provided with a non-slip coating.

So as to make the actuation of this clamping according to the aforementioned embodiment easy to perform, the at least one receptacle comprises a proximal wall section and a distal wall section, each having an extension component in the radial direction, wherein the proximal wall section in the direction of the distal end of the cutting sheath has a directional component that is directed radially away from the longitudinal axis, and the distal wall section has a directional component that is directed radially toward the longitudinal axis. This enables easy fixation and release, which in turn prevents uncontrolled sliding of the cutting sheath and thereby undesirable injuries.

This is preferably further facilitated if at least one of the two wall sections of the receptacle, and more preferably the proximal wall section, has an extension direction parallel to the first or second sections of the at least one clamping link of the at least one clamping device.

In a special embodiment, the locking sheath of the explantation device is still more preferably movably guided radially inside the cutting sheath in the lumen thereof, and the implanted lead can be introduced radially inside the locking sheath into the lumen thereof, so that the clamping device, by being displaced out of the receptacle into the lumen, which is adapted in terms of the inside diameter to the body of the locking sheath, is transferred into the clamped state, whereby the implanted lead is fixed.

An object is further achieved by a method for explanting implanted leads by means of an aforementioned explantation device, comprising the following steps:

a) introducing the proximal end of the implanted lead into the distal lumen openings of the cutting sheath and of the locking sheath of the explantation device, wherein the clamping device of the locking sheath is in the relaxed state in the receptacle of the cutting sheath and thereby the locking sheath is guided (even temporarily) with the cutting sheath;

b) advancing the explantation device in the direction of the distal end of the implanted lead and thereby detaching potentially present slightly adhering tissue adhesions on the implanted lead;

c) when meeting with strong adhesions or high resistance when advancing the explantation device in the direction of the distal end of the implanted lead: fixing the locking sheath so as to prevent a movement in relation to the implanted lead;

d) displacing the cutting sheath in the distal direction in relation to the locking sheath so that the clamping device is moved in the proximal direction out of the receptacle, wherein the locking sheath rigidly clamps with the implanted lead, and wherein the detaching unit of the cutting sheath detaches the strong adhesions from the implanted lead;

e) displacing the cutting sheath in the proximal direction in relation to the locking sheath so that the clamping device is moved in the distal direction into the receptacle, wherein the fixation of the locking sheath to the implanted lead is released; and f) optionally repeating steps c) to e) until the implanted lead is free of adhesions and can be removed from the body together with the explantation device.

Further features, aspects, objects, advantages, and possible applications of the present application will become apparent from a study of the exemplary embodiments and examples described below, in combination with the figures, and the appended claims.

DESCRIPTION OF THE DRAWINGS

The subject matter of the patent application will be described hereafter based on the enclosed drawings. In the drawings:

FIG. 1A is a longitudinal section view of a locking sheath according to a first embodiment of the present patent application;

FIG. 1B is a perspective illustration of the clamping device of the locking sheath in the relaxed state according to the first embodiment;

FIG. 1C is a perspective illustration of the clamping device of the locking sheath in the clamped state according to the first embodiment;

FIG. 2A is a longitudinal section view of a locking sheath according to a second embodiment of the present patent application;

FIG. 2B is a perspective illustration of the clamping device of the locking sheath in the relaxed state according to the second embodiment;

FIG. 2C is a perspective illustration of the clamping device of the locking sheath in the clamped state according to the second embodiment;

FIG. 4A is a longitudinal section view of the explantation device in the relaxed state in the first embodiment;

FIG. 4B is a longitudinal section view of the explantation device in the clamped state in the first embodiment;

FIG. 5A is a longitudinal section view of the explantation device in the relaxed state in the second embodiment;

FIG. 5B is a longitudinal section view of the explantation device in the clamped state in the second embodiment;

DETAILED DESCRIPTION

Figure 3A:
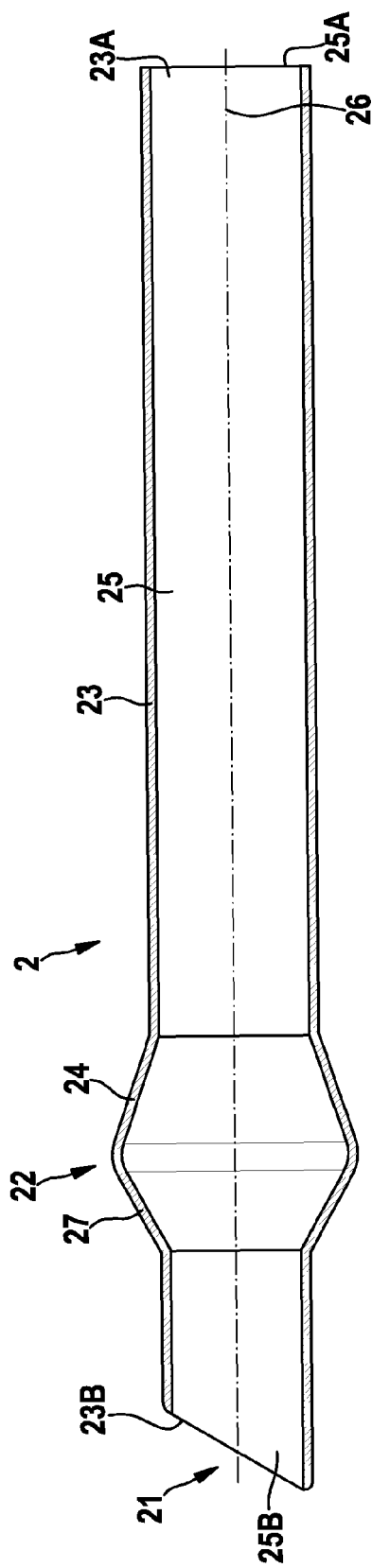
FIG. 3A depicts a cutting sheath according to an embodiment of the present patent application.

FIG. 1A shows a locking sheath 1 according to a first embodiment of the patent application. The locking sheath 1 comprises a hose-like or tubular body 16, which has a proximal end 16A and a distal end 16B and which extends along a longitudinal axis 18 and surrounds a lumen 17. The lumen 17 has an opening 17A and 17B at the proximal and distal ends, respectively. Both the lumen 17 and the openings 17A and 17B thereof are designed so as to allow an implanted lead to be introduced therein and displaceably mounted there.

The distal end of the locking sheath 1 is provided with a clamping device 11, which in FIG. 1A is shown in the relaxed state, in the extended distal opening 17B of the lumen 17. The clamping device 11 is used to temporarily fix a displaceably mounted implanted lead that is introduced into the lumen 17. In the shown relaxed state of the clamping device 11, it is possible to introduce the implanted lead into the lumen 17 or to push the locking sheath 1 over the implanted lead.

FIGS. 1B and 1C show perspective illustrations of the clamping device 11 of the locking sheath 1 in the relaxed state (FIG. 1B) and in the clamped state (FIG. 1C). The clamping device 11 is generally a collet, which comprises at least one, and preferably four, clamping links 12 extending in the direction of the longitudinal axis 18. In this embodiment, each clamping link 12 comprises a first section 13, which at the first end thereof is attached to the tubular body 16 and has an extension component that from the first end of the body toward the second end is directed away from the longitudinal axis 18. A second section 14, which projects away from the first section in the distal direction and is provided at the second end of the first section, has an extension component that is directed radially to the longitudinal axis 18 and an end 15 projecting radially in the direction of the longitudinal axis 18. In the relaxed state, this inwardly projecting end 15 is positioned so that it does not project into the interior of the lumen 17 or into the space in the extended lumen. In the relaxed state, no clamping action can thus be exerted on an implanted lead that is displaceably mounted in the lumen 17.

The inwardly projecting end 15 can be rounded, ground in an angled manner, roughened and ground as a blade and/or provided with a non-slip coating toward the end which can be brought into clamping engagement with the implanted lead.

The principle of the clamping device 11 will be explained hereafter based on one of the several clamping links 12. The principle, of course, applies to all clamping links 12 of a clamping device 11. When a radial pressure that is directed in the direction of the longitudinal axis 18 is exerted on the second end of the first section 13 which radially projects away from the longitudinal axis 18, which is to say the clamping device 11 is transferred from the state shown in FIGS. 1A and 1B into the clamped state shown in FIG. 1C, the end 15 of the second section 14 of the clamping link 12 which projects in the direction of the longitudinal axis is pushed inward, so that the end projects into the interior of the lumen 17 or into the space in the distally extended lumen. In this state, the end 15 engages with the implanted lead. The displaceably mounted implanted lead that was previously introduced in the locking sheath 1 is fixed relative to the locking sheath 1. When the aforementioned pressure acting on the second end of the first section 13 is removed again, the clamping link 12 returns to the relaxed state as a result of the spring force of the material and it is disengaged from the implanted lead. The implanted lead present in the lumen 17 of the locking sheath 1 can thus be grasped and released again. This principle can also be applied to other implants, for example, to a lead-bound implantable sensor or to a leadless pacer.

The embodiment of the locking sheath 1 shown in FIGS. 1A to 1C comprises a clamping device 11, which is designed such that the clamping links 12 are directed in the direction of the distal end 16B. This embodiment is easy to produce and, in the clamped state, applies slightly less damaging clamping action on the implanted lead, which can slide through the clamping device 11 above a certain tensile force.

A further embodiment of a locking sheath is shown in FIGS. 2A to 2C. The reference numerals shown therein denote the same features as the reference numerals shown in FIGS. 1A to 1C. Contrary to the embodiment shown in FIGS. 1A to 1C, the clamping device 11 of the locking sheath 1 is not attached in the extended distal opening 17B of the lumen 17, but instead offset in the proximal direction on the tubular body 16 of the locking sheath 1. The distal end 16B of the body 16 thus coincides with the distal opening 17B of the lumen. Because of this offset arrangement in the proximal direction, a different configuration of the clamping links 12 is possible. According to this embodiment, it is possible for the clamping links 12 not to be provided at the distal end 17B of the lumen 17, and instead to be provided in the proximal direction in front of the distal end 17B of the lumen 17. The remaining shaping of the clamping links 12, comprising a first 13 and a second 14 section, and the clamping device is identical to that described in FIG. 1A to FIG. 1C, however, the first section 13 is provided at the first end in the direction of the distal end 16B on the body 16 of the locking sheath 1.

This embodiment is a little more complicated to produce, however, the clamping action is considerably more effective in the pulling direction (in the direction of the proximal end 16A), because the ends 15 of the clamping links 12 which project in the direction of the longitudinal axis cut into the insulation of the implanted lead and thereby generate an additional opposing force.

The spring force of the bent clamping links 12 defines the force with which the implanted lead or the implant is grasped.

Figure 3B:
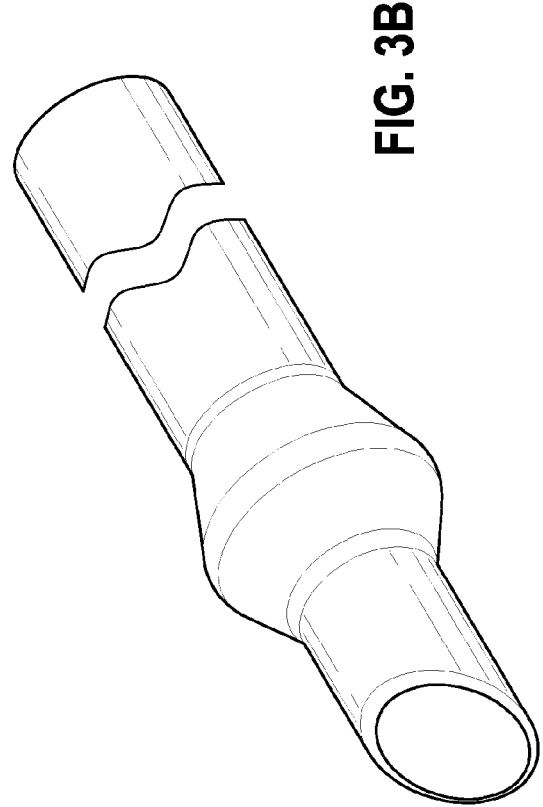
FIG. 3B is a longitudinal section view of the cutting sheath of FIG. 3A.

FIGS. 3A and 3B show a cutting sheath 2, with the aid of which not only the tissue is detached from the implanted lead, but also the clamping device 11 of the locking sheath is operated or triggered. The cutting sheath 2 for removing adhering tissue comprises a hose-like or tubular body 23 having a proximal 23A and a distal 23B end and a lumen 25 along a longitudinal axis 26 comprising openings 25A and 25B at the proximal and distal ends, respectively. A detaching unit 21 at, or in the vicinity of, the distal end 23B is designed to detach the adhering tissue from the implanted lead. This detaching unit is generally a blade, but different aforementioned units are also possible.

In a preferred embodiment, the cutting sheath 2 is designed and dimensioned so that the locking sheath 1 can be introduced in the lumen 25 and is displaceably mounted therein. The inside diameter of the lumen 25, however, is adapted to the outside diameter of the body 16 of the locking sheath 1, which means that the inside diameter 25 is considerably smaller than the outside diameter of the clamping device 11 which is formed by the second end of the first section 13, which from the first end thereof toward the second end is radially directed away from the longitudinal axis 18. This would keep the clamping device 11 constantly in the clamped state while the locking sheath 1 is introduced in a cutting sheath 2 of the conventional type. To allow activation and usage, the cutting sheath 2 comprises a receptacle 22 in the form of a recess in the distal section. The recess has a larger inside diameter than the body 23 of the cutting sheath 1. The inside diameter of the receptacle 22 generally corresponds at least substantially to the outside diameter of the clamping device 11. The receptacle 22 preferably comprises a proximal and a distal wall section 24 and 27. In this embodiment, both wall sections are inclined away from the longitudinal axis 26 or toward the longitudinal axis 26, which is to say they have an extension component parallel to the longitudinal axis, in addition to an extension component leading away from the longitudinal axis.

In the relaxed state of the clamping links 12, the clamping device 11 is located in the receptacle 22 and does not exert any clamping action on the implanted lead 3, which is introduced into the lumen of the locking sheath 1 and is displaceably mounted therein. This state is shown in FIGS. 4A and 5A. In this state, the user can handle the extraction device consisting of the cutting 2 and locking 1 sheaths like a known individual sheath, which is to say the device can be displaced relative to the implanted lead 3, for example, in order to detach slightly adhering tissue by means of the detaching unit 21 without opposing force, or only by means of the opposing force of a conventional locking stylet. In this position of the locking sheath 1, the device can also be pushed in the distal direction over the implanted lead 3 to the desired site at which the opposing force is to be applied.

The handling and mechanism of action of the device will now be described proceeding from the above description and proceeding from FIGS. 4A and 5A, based on the following description and FIGS. 4B and 5B. The latter FIGS. 4B and 5B show the state in which the clamping links 12 of the clamping device 11 are in the clamped state and exert a clamping action on the implanted lead 3. The clamping action is produced by displacing the cutting sheath 2 relative to the locking sheath 1, for example, in the direction of the arrow 4 in the distal direction, or by displacing the locking sheath 1 in relation to the cutting sheath 2 in the proximal direction. The clamping links 12 of the clamping device 11 slide out of the recess of the receptacle 22 into the lumen 25 of the body 23—the lumen 25 having a considerably smaller diameter than the outside diameter of the clamping device 11, whereby the radially inwardly projecting ends 15 of the clamping links 12 are deflected inward and pressed against the outer casing of the implanted lead 3. In the deflected state, each individual clamping link 12 of the clamping device 11 exerts a clamping action on the implanted lead 3, whereby the lead is fixed such that it can no longer be displaced in relation to the locking sheath 1. After fixation, the tissue which has adhered to the implanted lead 3 can be scraped off in the distal direction by means of the scraping unit 21 of the cutting sheath 2. The clamping device 11 always remains inside the lumen 25.

During an explantation, the clamping action can be removed any arbitrary number of times and re-applied, because it is necessary for the opposing force acting due to the clamping action of the clamping device 11 to be applied as closely in the vicinity of the scraping position as possible. So as to allow slight displacement of the locking sheath 1 in relation to the cutting sheath 2 from the relaxed state of the clamping device 11 into the clamped state, the two walls 24 (proximal) and 27 (distal) of the receptacle 22 are inclined away from the longitudinal axis 26 or toward the longitudinal axis 26, as illustrated in the Figures. The transfer into the clamped state of the clamping device 11 is notably facilitated when at least the wall 24 extends parallel to the proximal section. In the case of the embodiment shown in FIG. 4A and FIG. 4B, it is advantageous for the parallelism to exist between the proximal wall 24 and the first section 13 of the clamping link 12, and in the case of the embodiment shown in FIG. 5A and FIG. 5B, the parallelism advantageously exists between the wall 24 and the second section 14 of the clamping link 12.

All Figures show the inwardly projecting ends 15 of the clamping links 12 with no shape in order to illustrate the principle. As will be appreciated by one of ordinary skill in the art, the shape and design of the clamping links 12, however, can be adapted so as to improve the effect. It is conceivable for the inwardly projecting ends 15 to be rounded, ground in an angled manner, roughened and ground as a blade, or roughened and/or ground otherwise, and/or to provide them with a non-slip coating.

Depending on the requirement, both the spring action and the number of clamping links 12 may vary so as to act on implanted leads having various diameters.

According to a further embodiment, it is possible to combine the embodiment shown in FIG. 1A to FIG. 1C with the embodiment of FIGS. 2A to 2C and to dispose several clamping devices 11 behind one another and along the locking sheath 1. The associated cutting sheath 2 then comprises several receptacles 22 in which the clamping devices 11 rest in the relaxed state. The distance between two receptacles 22 can be the same as between the two associated clamping devices 11. The distance, however, can optionally also be different.

It is thus possible to activate the clamping action for differing displacement sections so as to apply or vary the opposing force step by step.

Both the locking sheath 1 of any of the aforementioned embodiments and the cutting sheath 2 can be produced from metals, in particular, for example, medical stainless steels or plastic materials (such as, for example, Teflon, PTFE, polypropylene, polyamide, PEABA, polyurethane or polyimide), or from a composition of different materials and/or different plastic materials.

To this end, it is also possible to provide visual markers, which indicate the position of the locking and cutting sheaths relative to each other, by any known imaging method (e.g., magnetic resonance imaging, ultrasound or X-ray). It is thus possible to determine whether the clamping device is in the relaxed state or in the clamped state.

Figure 6A:
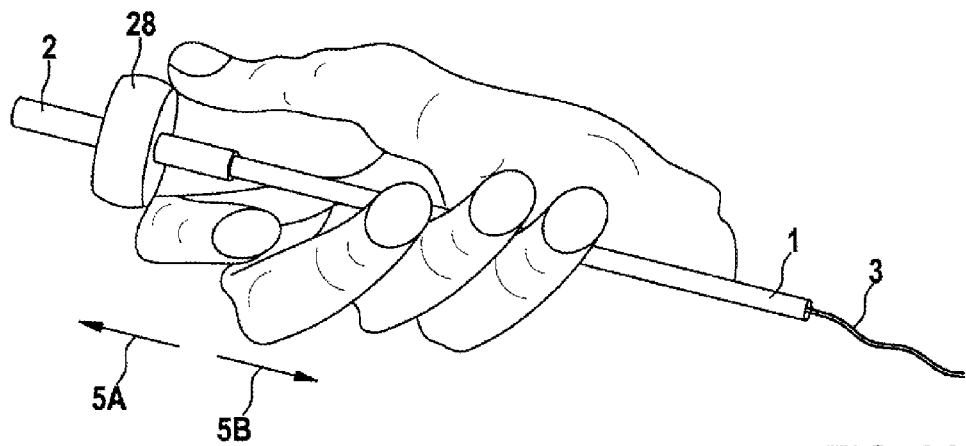
FIG. 6A is a perspective view of the proximal end of the explantation device, in which the collet is transferred from the relaxed state into the clamped state.
Figure 6B:
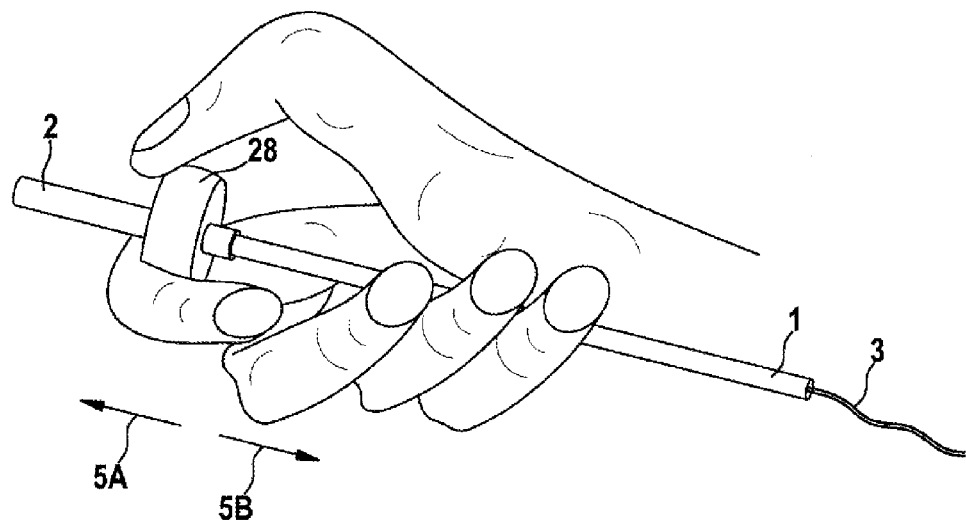
FIG. 6B is a perspective view of the proximal end of the explantation device, in which the collet is transferred from the clamped state into the relaxed state.

FIG. 6A and FIG. 6B show the proximal end of the explantation device consisting of the locking sheath 1 and the cutting sheath 2 according to any one of the aforementioned embodiments, which in both Figures are in the usage states of an advantageous embodiment in the hand of a surgeon or physician. In this embodiment, the explantation device is designed so that the locking sheath 1 is located between the implanted lead 3 present in the lumen 17 and the cutting sheath 2. The lengths of the two sheaths 1 and 2 are designed such that the locking sheath 1 proximally protrudes from the cutting sheath 2, preferably between 10 and 20 cm, so that the surgeon can grasp both sheaths simultaneously in one hand and can displace them in relation to each other (in directions of the arrows 5A and 5B).

The ends of both the locking sheath 1 and the cutting sheath 2 are advantageously designed so as to facilitate the grasping and mutual displacement. For example, it is possible to provide the proximal end of the cutting sheath 2 with a push device 28—for example, in the form of a thickened shaft region, a sliding handle, a sliding bead and/or a sliding button—which facilitates forward and backward sliding by means of the thumb and index finger, without changing the position of the locking sheath 1. In addition, the proximal end of the locking sheath 1 can be provided with a slip-resistant embossing (e.g., roughening) or a coating (for example silicone), which allows it to be held by hand during the relative displacement of the cutting sheath 2 (for applying an opposing force), but also facilitates gripping, pulling or sliding of the cutting sheath 2, using the thumb and index finger, relative to the locking sheath 1 held by the middle, ring and little fingers.

This advantageous proximal design of the two sheaths allows use by one hand. When an adhesion is reached, the clamping device 11 on the locking sheath 1 is moved from the relaxed state into the clamped state, in which the locking sheath 1 is held by means of the middle, ring and small fingers, while the thumb and index finger push the cutting sheath 2 in the distal direction (in direction of arrow 5A) by means of the thickened region 28 at the proximal end (FIG. 6A). When the adhesion has been detached, the clamping device 11 on the locking sheath 1 of the explantation device is transferred from the tensioned into the relaxed state (by pushing the cutting sheath 2 in the direction of arrow 5B), in which the cutting sheath 2 is retracted until the clamping device 11 slides into the receptacle 22 of the cutting sheath 2 and releases the implanted lead 3. For this purpose, the locking sheath 1 is held again, for example, by means of the middle, ring and small fingers, while the thumb and index finger retract the cutting sheath 2 with the aid of the thickened region 28 (FIG. 6B).

Moreover, a visual marker (for example, in the form of lines, images (icons), colors, etc.) can be present, for example, in the proximal end region of the locking sheath 2, the marker allowing the surgeon to ascertain what the tension state of the clamping jaw 11 is (relaxed or clamped state). For better handling, ergonomically shaped handles can be provided at the proximal end of the sheaths so as to make the displacement relative to each other easier.

As described above, the general use for the explantation device is shown in steps. The procedure, however, generally comprises further steps as follows:

a) dissecting the implanted lead and cutting off the connector of the implanted lead;

b) introducing the proximal end of the implanted lead into the distal lumen openings of the cutting sheath and of the locking sheath of the explantation device, wherein the clamping device of the locking sheath is located in the relaxed state in the receptacle of the cutting sheath, and thereby the locking sheath is guided (even temporarily) with the cutting sheath;

c) advancing the explantation device in the direction of the distal end of the implanted lead, and thereby detaching slightly adhering tissue adhesions on the implanted lead;

d) when meeting with strong adhesions or high resistance when advancing the explantation device in the direction of the distal end of the implanted lead: fixing the locking sheath so as to prevent a movement in relation to the implanted lead;

e) displacing the cutting sheath in the distal direction in relation to the locking sheath so that the clamping device moves in the proximal direction out of the receptacle, wherein the locking sheath rigidly clamps with the implanted lead, and wherein the detaching unit of the cutting sheath detaches the strong adhesions from the implanted lead;

f) displacing the cutting sheath in the proximal direction in relation to the locking sheath so that the clamping device moves in the distal direction into the receptacle, wherein the fixation of the locking sheath to the implanted lead is released; and g) optionally repeating steps c) to f) until the implanted lead is free of adhesions and can be removed from the body together with the explantation device.

For implanted leads having a guide wire lumen, there is also the option of the using them additionally with the aid of a locking stylet. In this case, the explantation method with the aid of the explantation device generally comprises the following steps:

a) dissecting the implanted lead and cutting off the connector of the implanted lead;

b) introducing and anchoring the locking stylet in the guide wire lumen of the implanted lead;

c) introducing the proximal end of the implanted lead, along with the locking stylet introduced therein, in the distal lumen openings of the cutting sheath and of the locking sheath of the explantation device, wherein the clamping device of the locking sheath is located in the relaxed state in the receptacle of the cutting sheath, and thereby the locking sheath is guided (even temporarily) with the cutting sheath;

d) advancing the explantation device in the direction of the distal end of the implanted lead, and thereby detaching slightly adhering tissue adhesions on the implanted lead;

e) when meeting with strong adhesions or high resistance when advancing the explantation device in the direction of the distal end of the implanted lead: fixing the locking sheath so as to prevent a movement in relation to the implanted lead;

f) displacing the cutting sheath in the distal direction in relation to the locking sheath so that the clamping device moves in the proximal direction out of the receptacle, wherein the locking sheath rigidly clamps with the implanted lead, and wherein the detaching unit of the cutting sheath detaches the strong adhesions from the implanted lead;

g) displacing the cutting sheath in the proximal direction in relation to the locking sheath so that the clamping device moves in the distal direction into the receptacle, wherein the fixation of the locking sheath to the implanted lead is released; and h) optionally repeating steps d) to g) until the implanted lead is free of adhesions and can be removed from the body together with the explantation device.

When advancing and removing the tissue, it is also possible to perform a rotary motion about the longitudinal axis with the entire explantation device (in the case of slight adhesions) or with the cutting sheath only, so as to bring about an additional detachment effect. The detachment effect can also be amplified by repeating the brief forward and backward sliding of the explantation device several times.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention. Additionally, the disclosure of a range of values is a disclosure of every numerical value within that range.

I claim:

1. An explantation device for explanting implanted leads, having a distal end pointing in the direction of the explantation site and a proximal end pointing in the direction of the surgeon, the explantation device comprising:

a locking sheath for releasably fastening to an implanted lead, the locking sheath comprising a hose-like or tubular body having a distal end and a proximal end and a lumen along a longitudinal axis which has an opening both at the distal end and at the proximal end, and further comprising at least one clamping device at or in the vicinity of the distal end, wherein the clamping device can be transferred from a relaxed state into a clamped state and back into the relaxed state; and a cutting sheath for removing adhering tissue, the cutting sheath comprising a hose-like or tubular body having a proximal end and a distal end with a lumen along a longitudinal axis designed and dimensioned so that the locking sheath is introduced in the lumen of the cutting sheath and is displaceably mounted therein, the lumen having an opening both at the proximal end and at the distal end, and further comprising a detaching unit at or in the vicinity of the distal end, the cutting sheath being freely movably in relation to the locking sheath along the longitudinal axis;

wherein the cutting sheath comprises at least one receptacle for the clamping device of the locking sheath, the receptacle being designed so as to receive the clamping device therein in the relaxed state of the clamping device;

wherein in the clamped state the at least one clamping device causes fixation of the locking sheath to the implanted lead and in the relaxed state releases the fixation of the locking sheath to the implanted lead, wherein the transfer from the relaxed state into the clamped state, and from the clamped state into the relaxed state, takes place with utilization of a spring force, by displacing the cutting sheath, and hence the at least one receptacle, along the longitudinal axis in relation to the locking sheath so that the at least one clamping device moves out of or into the at least one receptacle;

wherein the locking sheath is guided with the cutting sheath when the at least one clamping device is present in the at least one receptacle;

wherein the at least one clamping device is a collet, which comprises at least one clamping link extending in a direction of the longitudinal axis, wherein each clamping link comprises a first section, which at a first end is attached to the locking sheath, and a second section having an end projecting radially in the direction of the longitudinal axis;

wherein the at least one receptacle comprises a proximal wall section and a distal wall section, each having an extension component in the radial direction of the longitudinal axis, wherein the proximal wall section in a direction of the distal end of the cutting sheath has a directional component that is directed radially away from the longitudinal axis and the distal wall section has a directional component that is directed radially toward the longitudinal axis; and wherein at least one of the proximal wall section and the distal wall section has a respective extension direction parallel to the first or second sections of the at least one clamping link of the at least one clamping device.

2. The explantation device according to claim 1, wherein the at least one clamping device and the at least one receptacle have at least one respective radial extension component.

3. The explantation device according to claim 1, wherein the at least one clamping device comprises four clamping links.

4. The explantation device according to claim 1, wherein the first section of the least one clamping link, in the relaxed state, has an extension component that from the first end of the section toward a second end is directed radially away from the longitudinal axis, and the second section projects away from the first section in the distal direction and is provided at the second end of the first section to form an inwardly projecting end.

5. The explantation device according to claim 1, wherein the inwardly projecting end projects into the lumen in the clamped state.

6. The explantation device according to any claim 1, wherein the inwardly projecting end is rounded, ground in an angled manner, roughened and ground in the form of a blade, and/or provided with a non-slip coating.

7. The explantation device according to claim 1, wherein the locking sheath is movably guided radially inside the cutting sheath in the lumen thereof and the implanted lead can be introduced radially inside the locking sheath in the lumen, so that the clamping device by displacement out of the receptacle into the lumen, which is adapted in terms of the inside diameter to the body of the locking sheath, is transferred into the clamped state, whereby the implanted lead is fixed.

8. A method for explanting implanted leads by means of an explantation device according to claim 1, comprising the following steps:
   a) introducing a proximal end of the implanted lead, along with a locking stylet introduced therein, into the distal lumen openings of the cutting sheath and of the locking sheath of the explantation device, wherein the clamping device of the locking sheath is located in the relaxed state in the receptacle of the cutting sheath and thereby the locking sheath is guided with the cutting sheath;
   b) advancing the explantation device in a direction of a distal end of the implanted lead and thereby detaching slightly adhering tissue adhesions on the lead;
   c) when meeting with strong adhesions or high resistance when advancing the explantation device in the direction of the distal end of the implanted lead: fixing the locking sheath so as to prevent a movement in relation to the implanted lead;
   d) displacing the cutting sheath in the distal direction in relation to the locking sheath so that the clamping device moves in the proximal direction out of the receptacle, wherein the locking sheath rigidly clamps with the implanted lead, and wherein the detaching unit of the cutting sheath detaches the strong adhesions from the implanted lead;
   e) displacing the cutting sheath in the proximal direction in relation to the locking sheath so that the clamping device moves in the distal direction into the receptacle, wherein the fixation of the locking sheath to the implanted lead is released; and
   f) optionally repeating steps b) to e) until the implanted lead is free of adhesions and can be removed from the body together with the explantation device.

* * * * *